United States Patent
Ceccaldi et al.

(10) Patent No.: US 10,733,788 B2
(45) Date of Patent: Aug. 4, 2020

(54) DEEP REINFORCEMENT LEARNING FOR RECURSIVE SEGMENTATION

(71) Applicant: Siemens Healthcare GmbH, Erlangen (DE)

(72) Inventors: Pascal Ceccaldi, Princeton, NJ (US); Xiao Chen, Princeton, NJ (US); Boris Mailhe, Plainsboro, NJ (US); Benjamin L. Odry, West New York, NJ (US); Mariappan S. Nadar, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/251,242

(22) Filed: Jan. 18, 2019

(65) Prior Publication Data
US 2019/0287292 A1    Sep. 19, 2019

Related U.S. Application Data

(60) Provisional application No. 62/643,348, filed on Mar. 15, 2018.

(51) Int. Cl.
*G06T 15/08* (2011.01)
*G01R 33/56* (2006.01)
(Continued)

(52) U.S. Cl.
CPC ............ *G06T 15/08* (2013.01); *A61B 6/5205* (2013.01); *G01R 33/5608* (2013.01); *G06N 3/084* (2013.01); *G06N 20/00* (2019.01); *G06T 7/0012* (2013.01); *G06T 2207/10088* (2013.01); *G06T 2207/20081* (2013.01); *G06T 2207/30016* (2013.01)

(58) Field of Classification Search
CPC ......... G06T 15/08; G06T 7/00; G06T 7/0012; G06T 2207/20081; G06T 2207/10088; G06T 2207/30016; G01R 33/5608; G01R 33/56; A61B 6/5205; A61B 6/00; A61B 5/055; A61B 5/7267; A61B 6/032; A61B 5/4836; A61B 5/7264; G06N 3/08; G06N 20/00; G06N 3/084
See application file for complete search history.

(56) References Cited

U.S. PATENT DOCUMENTS

| 8,068,655 | B2 | 11/2011 | Odry et al. | |
| 2010/0027865 | A1* | 2/2010 | Wels | G06K 9/4614 382/131 |

(Continued)

FOREIGN PATENT DOCUMENTS

| WO | 2016014354 A1 | 1/2016 |
| WO | 2017023569 A1 | 2/2017 |

*Primary Examiner* — Xilin Guo

(57) ABSTRACT

Systems and methods are provided for generating segmented output from input regardless of the resolution of the input. A single trained network is used to provide segmentation for an input regardless of a resolution of the input. The network is recursively trained to learn over large variations in the input data including variations in resolution. During training, the network refines its prediction iteratively in order to produce a fast and accurate segmentation that is robust across resolution differences that are produced by MR protocol variations.

19 Claims, 8 Drawing Sheets
(1 of 8 Drawing Sheet(s) Filed in Color)

(51) Int. Cl.
*A61B 6/00* (2006.01)
*G06T 7/00* (2017.01)
*G06N 20/00* (2019.01)
*G06N 3/08* (2006.01)

(56) References Cited

U.S. PATENT DOCUMENTS

| | | |
|---|---|---|
| 2016/0247299 A1 | 8/2016 | Tan |
| 2017/0371017 A1 | 12/2017 | Odry et al. |
| 2017/0372193 A1* | 12/2017 | Mailhe ................. G06N 3/0472 |
| 2018/0161986 A1* | 6/2018 | Kee .................... G06K 9/00664 |
| 2019/0108441 A1* | 4/2019 | Thibault .................. G06N 3/08 |
| 2019/0236411 A1* | 8/2019 | Zhu ..................... G06K 9/4628 |

* cited by examiner

DEEP REINFORCEMENT LEARNING FOR RECURSIVE SEGMENTATION

CROSS REFERENCE TO RELATED APPLICATIONS

This application claims the benefit of U.S. Provisional Application No. 62/643,348, filed Mar. 15, 2018, which is hereby incorporated by reference in its entirety.

FIELD

The present embodiments relate to medical image processing.

BACKGROUND

The rapid development of noninvasive brain imaging technologies has opened new horizons in analyzing and studying the anatomy and function of the body. In an example, progress in accessing brain injury and exploring brain anatomy has been made using magnetic resonance (MR) imaging. The advances in brain MR imaging have also provided data with an increasingly high level of quality. The analysis of the MR datasets has become a tedious and complex task for clinicians, who have to manually extract important information. This manual analysis is often time-consuming and prone to errors. More recently, computerized methods for MR image segmentation, registration, and visualization have been extensively used to assist doctors and clinicians in qualitative diagnosis.

The medical imaging environment is highly diverse in terms of data acquisition, contrast or resolution. Brain Segmentation for instance, is a standard preprocessing step for neuroimaging applications, often used as a prerequisite for anomaly detection, tissue segmentation, and morphometry applications. Brain MR segmentation is an essential task in many clinical applications because it influences the outcome of the entire analysis. This is because different processing steps rely on accurate segmentation of anatomical regions. For example, MR segmentation is commonly used for measuring and visualizing different brain structures, for delineating lesions, for analyzing brain development, and for image-guided interventions and surgical planning. Each clinical application may require or use different resolutions or dimensions. To perform the segmentation task, each clinical application may thus require a dedicated segmentation application or network.

Automating brain segmentation is challenging due to the sheer amount of variations of brain shapes and sizes as well as variation in imaging. Protocol differences in MR acquisition may lead to variations in image resolution. In an example, a first medical imaging scan may use a first resolution while a second medical imaging scan may use a second resolution. The resolutions or dimensions of the resulting images or volumes may be different due to the intended use of the imaging, making automated brain segmentation less reliable.

SUMMARY

By way of introduction, the preferred embodiments described below include methods and systems for generating and applying a single trained network for segmentation of MR data regardless of the resolution of the MR data. The network is trained reclusively using machine learning techniques. The resolution of the input to the network is adjusted up or down. Feature maps generated by the network are applied to the inputs of the next iteration. The network is trained to be robust given different resolution input MR images or volumes.

In a first aspect, a method is provided for generating segmented magnetic resonance volumes in a magnetic resonance imaging system. A patient is scanned by the magnetic resonance imaging system; magnetic resonance volume data resulting from the scanning. The magnetic resonance volume data is input to a trained network that is recursively trained to generate segmented volumes from input magnetic resonance volume data regardless of a resolution of the input magnetic resonance volume data. The trained network generates a segmented magnetic resonance volume from the input magnetic resonance volume data. The segmented magnetic resonance volume is displayed.

In a second aspect, a method is provided for training a network to generate segmented magnetic resonance images regardless of input resolution. An MR image of a plurality of MR images of a set of training data is input into a network using a first quantity of input channels. The quantity is equal to the quantity of classifications provided by the network. The network generates a segmented image including the quantity of probability maps. The segmented image is compared to a ground truth segmented image for the MR image. The network is adjusted based on the comparison. A reinforcement agent selects a resolution action as a function of the comparison. Each of the first quantity of input channels of the MR image are multiplied by a respective probability map of the quantity of probability maps. The resolution action is performed on the MR images for each of the quantity of input channels. The altered MR images of the quantity of input channels are input into the network. Generating, comparing, adjusting, selecting, multiplying, performing, and inputting are repeated for at least five iterations. The trained network is output.

In a third aspect, a system is provided generating a trained network configured to use inputs of different resolutions. The system includes a magnetic resonance imaging system, a memory, and an image processor. The magnetic resonance imaging system is configured to acquire magnetic resonance data at different resolutions.

The memory is configured to store the magnetic resonance data, associated labeled magnetic resonance data, and the network. The image processor is configured to recursively train the network using an input volume from the magnetic resonance data and an associated labeled volume using back propagation. The network generates probability maps from a SoftMax activation layer at each iteration of the recursive training. The input volume is up sampled or pooled to different resolutions for each iteration. After each iteration, the probability maps are multiplied with the input volume and input back to the network. The recursive training is repeated for each volume in the magnetic resonance data.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The components and the figures are not necessarily to scale, emphasis instead being placed upon illustrating the principles of the invention. Moreover, in the figures, like reference numerals designate corresponding parts throughout the different views.

DETAILED DESCRIPTION

A single trained network is used to provide segmentation for an input regardless of a resolution of the input. A network is recursively trained using machine learning techniques to learn over large variations in the input data including variations in resolution. During training, the network refines its prediction iteratively in order to produce a fast and accurate segmentation that is robust across resolution differences that are produced by MR protocol variations.

One field where segmentation is important is in the field of medical imaging. In image processing, segmentation is the process of dividing an input into different parts or sections. One field that values accurate segmentation is MR image processing. Methods for initial MR analysis fall into two general categories: classification and segmentation. Classification assigns a label to an MR series, e.g. normal or abnormal, level of severity, or a diagnosis. Segmentation is the process of delineating the boundaries, or contours, of various tissues. Image segmentation may be performed on two dimensional images, sequences of two-dimensional images, three-dimensional volume, or sequences of three-dimensional volumes. If the data is defined in three-dimensional space (e.g., obtained from a series of MR images), each image slice may be segmented individually in a slice-by-slice manner. The two-dimensional slices are then connected into a 3D volume or a continuous surface. Alternatively, the segmentation is of the volume rather than slice-by-slice.

Figure 1:
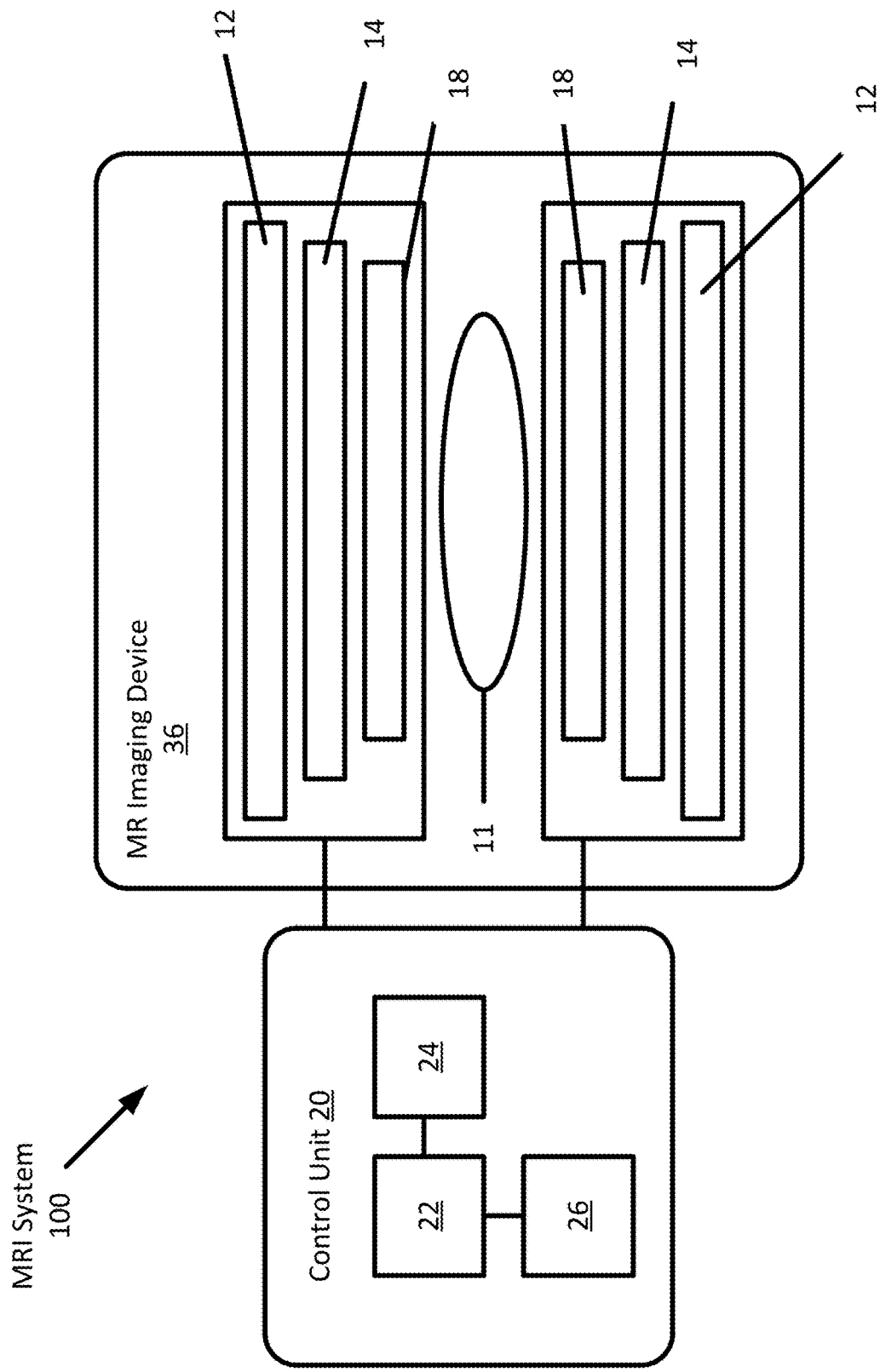
FIG. 1 depicts an example MR system.

FIG. 1 depicts an MR system 100 for acquisition of frequency domain components representing MR image data for storage in a storage array. The MR system 100 includes a control unit 20 configured to process the MR signals and generate images of the body for display to an operator. The control unit 20 may store the MR signals and images in a memory 24 for later processing or viewing. The control unit 20 may include a display 26 for presentation of images to an operator. The MR scanning system 100 is only exemplary, and a variety of MR scanning systems may be used to collect the MR data.

In the MR system 100, magnetic coils 12 create a static base or main magnetic field in the body of patient 11 or an object positioned on a table and imaged. Within the magnet system are gradient coils 14 for producing position dependent magnetic field gradients superimposed on the static magnetic field. Gradient coils 14, in response to gradient signals supplied thereto by a gradient and control unit 20, produce position dependent and shimmed magnetic field gradients in three orthogonal directions and generate magnetic field pulse sequences. The shimmed gradients compensate for inhomogeneity and variability in an MR imaging device magnetic field resulting from patient anatomical variation and other sources.

The control unit 20 may include a RF (radio frequency) module that provides RF pulse signals to RF coil 18. The RF coil 18 produces magnetic field pulses that rotate the spins of the protons in the imaged body of the patient 11 by ninety degrees or by one hundred and eighty degrees for so-called "spin echo" imaging, or by angles less than or equal to 90 degrees for "gradient echo" imaging. Gradient and shim coil control modules in conjunction with RF module, as directed by control unit 20, control slice-selection, phase-encoding, readout gradient magnetic fields, radio frequency transmission, and magnetic resonance signal detection, to acquire magnetic resonance signals representing planar slices of the patient 11.

In response to applied RF pulse signals, the RF coil 18 receives MR signals, e.g. signals from the excited protons within the body as the protons return to an equilibrium position established by the static and gradient magnetic fields. The MR signals are detected and processed by a detector within RF module and the control unit 20 to provide an MR dataset to an image data processor 22 for processing into an image. In some embodiments, the image data processor 22 is located in the control unit 20, in other embodiments, the image data processor 22 is located remotely. A two or three-dimensional k-space storage array of individual data elements in a memory 24 of the control unit 20 stores corresponding individual frequency components including an MR dataset. The k-space array of individual data elements includes a designated center, and individual data elements individually include a radius to the designated center.

A magnetic field generator (including coils 12, 14 and 18) generates a magnetic field for use in acquiring multiple individual frequency components corresponding to individual data elements in the storage array. The individual frequency components are successively acquired using a Cartesian acquisition strategy as the multiple individual frequency components are sequentially acquired during acquisition of an MR dataset. A storage processor in the control unit 20 stores individual frequency components acquired using the magnetic field in corresponding individual data elements in the array. The row and/or column of corresponding individual data elements alternately increases and decreases as multiple sequential individual frequency components are acquired. The magnetic field acquires individual frequency components in an order corresponding to a sequence of substantially adjacent individual data elements in the array, and magnetic field gradient change between successively acquired frequency components is substantially minimized.

One use of MR imaging is in studying a patient's brain. Steps for analysis generally include the classification of acquired MR data into specific tissue types and the identification and description of specific anatomical structures. Classification may assign to each element in the image a tissue class when the classes are defined in advance. In the case of brain MR, for tissue classification, image elements may be classified into three main tissue types: white matter (WM), gray matter (GM), and cerebrospinal fluid (CSF). Classification of the tissue types requires segmentation of the MR data into different parts. The segmentation results may also be used in different applications such as for analyzing anatomical structures, for studying pathological regions, for surgical planning, and for visualization.

In addition to classification of the brain material, segmentation may be used to preprocess MR data so that further analysis or segmentation may be performed. MR brain scan data generally includes some non-brain tissues such as skin, fat, muscle, neck, and eye balls. The presence of the non-brain tissues is an obstacle for further automatic brain image segmentation and analysis. A preliminary preprocessing step may be required to isolate the brain from extra-cranial or non-brain tissues. The preliminary preprocessing step is commonly referred to as skull stripping. Brain images that are preprocessed with skull stripping typically lead to better segmentation and classification of different brain regions that results in better and more accurate diagnosis of various brain-related diseases. Skull stripping may also be used as a preprocessing step prior to other image processing algorithms such as image registration and warping, brain volumetric measurement, inhomogeneity correction, tissue classification, analysis of cortical structure, cortical surface reconstruction, cortical thickness estimation, identification of brain parts, multiple sclerosis analysis, Alzheimer's disease, schizophrenia, and monitoring the development or aging of the brain among other uses.

One issue with both segmentation and skull stripping is the inputs vary in resolution and dimensions. MR image acquisition is highly diverse in terms of data acquisition, contrast or resolution. For skull stripping, in particular, the end uses may vary and as such use different sized images or volumes as inputs. Different protocols and machines may be used to acquire the MR data depending on the intended use. In an example, a first protocol may use a resolution of 256×256×256 while a second protocol may use a resolution of 128×128×32. Classical supervised ML does not adequately handle this real-world data problem. Each different resolution may require a separate network trained exclusively on training data that is the appropriate resolution. As there are numerous different resolutions, this may require numerous networks and training sessions. This also may require additional, difficult to locate in sufficient numbers, ground truth data to train the numerous networks.

Embodiments provide a supervised deep machine learning (ML) approach to train a single network to be robust across volume resolution while providing segmentation. Embodiments provide a combined method of supervised deep learning, deep reinforcement learning and recursive learning to provide a single trained network that may be used for inputs of varying resolution. The disclosed trained network may be implemented to computationally facilitate processing of medical imaging data and consequently improving and optimizing medical diagnostics. By using a single network that is robust across multiple resolutions, errors are diminished and outcomes are improved. The use of a single network is efficient in that fewer resources are used to both train and store a single network as opposed to multiple networks for multiple resolutions. The use of a single network further limits errors by removing a selection step and allowing clinicians or physicians to use a single pathway from MR imaging to analysis for the given application (e.g., brain scan).

Figure 2:
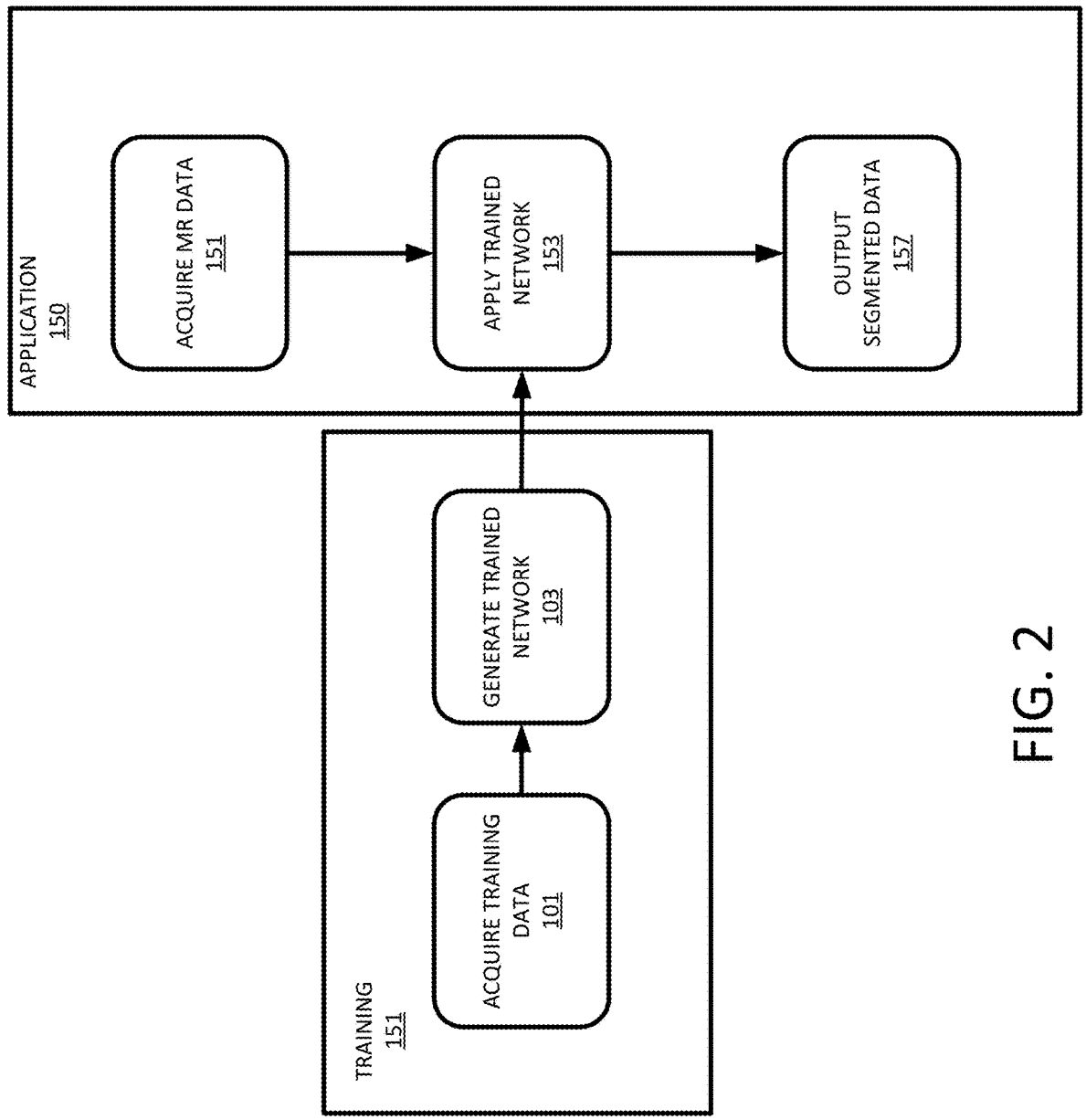
FIG. 2 depicts an example workflow for training and applying a trained network.

FIG. 2 depicts an example flowchart for providing resolution independent image processing for a magnetic resonance imaging system. The flowchart includes two stages, a training stage 151 for generating or training the network using a collection of training data (labeled data) and an application stage 150 for applying the generated/trained network to new unseen (unlabeled) data. The training stage 151 includes acquiring 101 training data and inputting the training data into a network in order to generate 103 a trained network. The output is a trained network that is applied 153 in the application stage 150. The application stage 150 includes acquiring 151 unseen MR data, applying 153 the trained network that was trained during the training stage 151, and outputting 157 segmented data.

The training stage 151 and application stages 150 are described in detail below at FIGS. 3 and 6, respectively. The training stage 151 may be performed at any point prior to the application stage. The training stage 151 may be repeated after new training data is acquired. The application stage 150 may be performed at any point after the training stage 151 generates the trained network and MR data is acquired. The application stage 150 may be performed, for example, during (e.g. real time) or directly after a medical procedure is performed or as part of planning for a particular patient. Alternatively, the application stage 150 may be performed at a later point using MR data acquired from an imaging scan and stored, for example, in a PACS.

The embodiments below use brain segmentation (skull stripping) as an example of the application of the trained network. The trained network may be applied to any segmentation problem found in medical imaging or other fields when provided with appropriate training data. The trained network provides accurate segmentation regardless of the resolution of the input image or volume.

Figure 3:
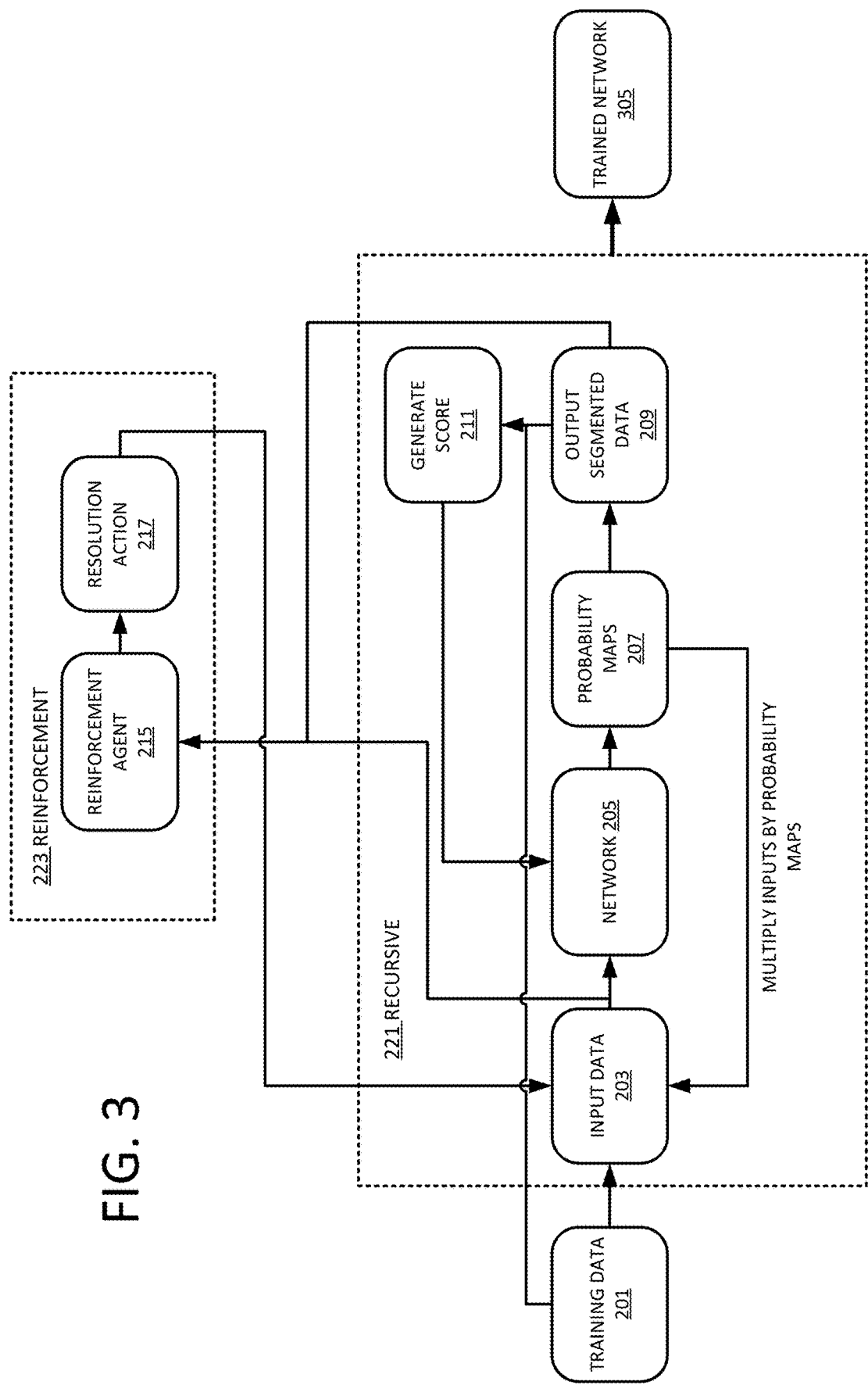
FIG. 3 depicts an example workflow for recursively training a network.

FIG. 3 depicts an example flowchart for generating a resolution robust trained network 305 using machine learning. The trained network 305 may be a machine learned network 305 or machine trained network 305. The trained network 305 is trained using a supervised training method. Unlabeled training data 201 is input into the network 205 that generates an outcome that is compared against associated labeled training data 201. Using backpropagation and a gradient, the network 205 adjusts internal parameters based on the comparison. The process is repeated until the network 205 may no longer be improved or a set point is reached. The training process for the network 205 may include both recursive learning 221 and reinforcement learning 223.

Figure 8:
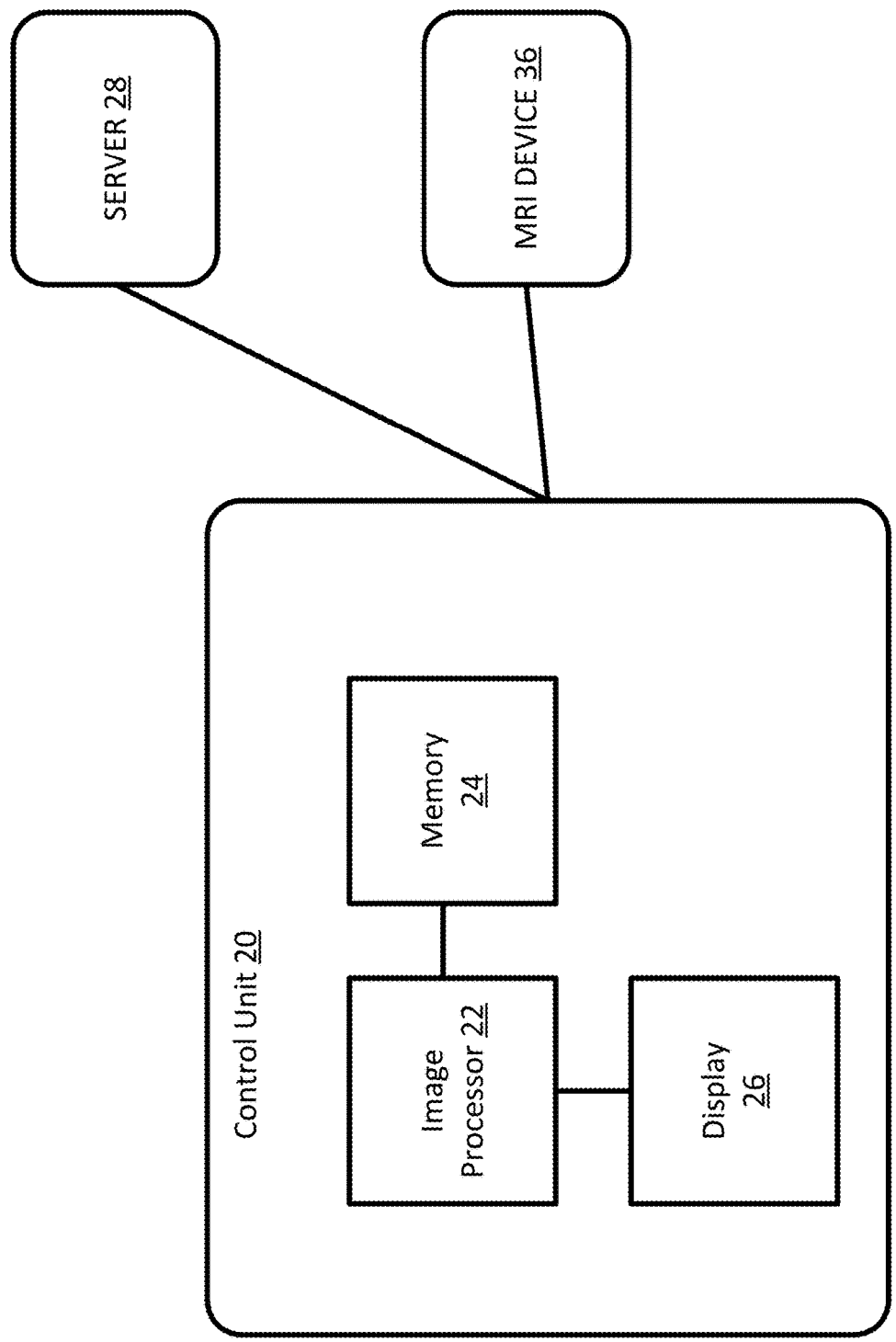
FIG. 8 depicts a system for training and applying a recursively trained network.

The acts are performed by the system of FIG. 1, FIG. 3, FIG. 8, other systems, a workstation, a computer, and/or a server. Additional, different, or fewer acts may be provided. The acts are performed in the order shown (e.g., top to bottom) or other orders.

At 201, training data 201 is acquired. Training data 201 may include ground truth data or gold standard data. Ground truth data and gold standard data is data that includes correct or reasonably accurate labels. For the segmentation problem, the training data 201 includes the original data and associated segmented data. Labels for segmentation purposes include labels for each voxel in the segmented data, an outline, or a fit shape. The segmented data may be generated and labeled using any method or process, for example, manually by an operator or automatically by one or more automatic methods. Different training data 201 may be acquired for different segmentation tasks. For example, a first set of training data 201 may be used to train a first network 205 for segmenting brain data, while a second set of training data 201 may be used to train a second network 205 for segmenting heart data. The training data 201 may be acquired at any point prior to inputting the training data 201 into the network 205. The training data 201 may include volumes of different resolutions or contrast. The training data 201 may be updated after acquiring new data. The updated training data 201 may be used to retrain or update the network 205.

In an embodiment, the training data 201 is MR data. As used herein, MR data includes both raw MR data and processed MR data. Processed MR data may include image and volume data. MR data may include 2D images, sequences of 2D images, 3D volumetric imagery, or sequence of 3D volumetric imagery. If the MR data is defined in 3D space (e.g., obtained from a series of MR images), each image "slice" may be provided individually in a "slice-by-slice" manner. Alternatively, the MR data may be provided as 3D volumetric data directly to the network 205. The examples described herein use three-dimensional MR data referred to as volumes. Volumes are encoded using an array of elements referred to as voxels. A voxel represents a value on a regular grid in three-dimensional space. The methods and systems described below may also be used with two-dimensional MR data referred to as images. An image is encoded using a bitmap of pixels.

At 203, a volume from the training data 201 is input to the network 205 using a first number of input channels. For an initial state, the same MR volume data may be used for a plurality of input channels to the network 205. For subsequent iterations, the MR volume data is multiplied by the output probability maps 207 of the network 205. The number of input channels is equal to the number of classes provided by the network 205. As an example, if the network 205 is configured to generate two classes (e.g. brain and non-brain material), the network 205 is then configured to use two input channels. A first input channel is multiplied by the brain probability map and the second input channel is multiplied by the non-brain probability map.

The initial MR volume data (for an initial state) or the adjusted MR volume data (for subsequent states) is input into the network 205. The network 205 is configured to segment the input volume data. Segmentation separates different portions from one another. In the example of skull stripping, non-brain tissues such as fat, skull, or neck may include intensities that overlap with intensities of brain tissues. The brain tissue may be identified before further processing may be performed. Segmentation for skull stripping classifies voxels as brain or nonbrain. The result may either be a new volume with just brain voxels or a mask, that includes, for example, a value of 1 for brain voxels and 0 for the rest of tissues. In general, the brain voxels include GM, WM, and CSF of the cerebral cortex and subcortical structures, including the brain stem and cerebellum. The scalp, dura matter, fat, skin, muscles, eyes, and bones are classified as nonbrain voxels.

The network 205 generates probability maps 207 for each of the classes. A probability map 207 may include a value that represents an estimation by the network 205 whether or not each voxel represents the respective class. The probability maps 207 may be generated using a SoftMax activation layer at the output of the network 205. The SoftMax activation layer takes an un-normalized vector from the network 205, and normalizes the vector into a probability distribution. The probability maps 207 that are generated by the network 205 are used to generate the output segmented volume. Combined, the probability maps 207 represent a probability for each of the classes for each voxel. For each voxel, the most probable class may be selected and the voxel thus assigned to the class. In an example, for a two-class segmentation, there are two probability maps 207, that when combined provide probability for each of the voxels to be one or the other class. The output data may be visualized as a two-colored volume where each voxel is colored with the respective class for which it is assigned the highest probability.

The output segmented data 209 is compared against the ground truth of the training data 201 to determine a score 211. The score 211 may represent the level of differences between the output segmented data 209 and the correct segmented data (ground truth or gold standard) provided with the training data 201. The score 211 is used to adjust weights of the network 205 using backpropagation and a gradient.

The score 211 may be calculated as a dice score that is calculated as:

$$\frac{|P \cap T|}{(|P| + |T|)/2}$$

where P represents the segmented area and T represents the ground truth area. Dice scores range from 0 to 1, where a score of 1 represents perfect segmentation. Other scores, errors, or loss functions may be used.

In an embodiment, the network 205 may be configured as a DenseNet. The DenseNet connects each layer to every other layer in a feed-forward fashion. For each layer in the DenseNet, the feature-maps of all preceding layers are used as inputs, and the output feature-map of that layer is used as input into all subsequent layers. In the DenseNet, for each layer, the feature maps of all preceding layers are used as inputs, and its own feature maps are used as inputs into all subsequent layers. To reduce the size of the network, the DenseNet may include transition layers. The layers include convolution followed by average pooling. The transition layers reduce height and width dimensions but leave the feature dimension the same. The final layer may be a SoftMax activation layer that generates the probability maps 207 used in generating an input for a subsequent iteration. The ML generator network may further be configured as a U-net. The U-Net is an encoder-decoder combination in which the outputs from the encoder-half of the network are concatenated with the mirrored counterparts in the decoder-half of the network. Skip connections between the encoder and decoder at any level of resolution greater than the bottleneck may be used.

Other network configurations may be used, such as deep architectures including convolutional neural network (CNN) or deep belief nets (DBN). CNN learns feed-forward mapping functions while DBN learns a generative model of data. In addition, CNN uses shared weights for all local regions while DBN is a fully connected network (e.g., including different weights for all regions of an image). The training of CNN is entirely discriminative through back-propagation. DBN, on the other hand, employs the layer-wise unsupervised training (e.g., pre-training) followed by the discriminative refinement with back-propagation if necessary. In an embodiment, the arrangement of the network 205 is a fully convolutional network (FCN). Alternative network arrangements may be used, for example, a 3D Very Deep Convolutional Networks (3D-VGGNet). VGGNet stacks many layer blocks containing narrow convolutional layers followed by max pooling layers. A 3D Deep Residual Networks (3D-ResNet) architecture may be used. A Resnet uses residual blocks and skip connections to learn residual mapping.

For each network configuration, rather than pre-programming the features and trying to relate the features to attributes, the deep architecture of the network is defined to learn the features at different levels of abstraction based on an input data with or without pre-processing. The features are learned to reconstruct lower level features (i.e., features at a more abstract or compressed level). For example, features for reconstructing an image are learned. For a next unit, features for reconstructing the features of the previous unit are learned, providing more abstraction. Each node of the unit represents a feature. Different units are provided for learning different features.

In an embodiment, the network 205 is a three-dimensional image-to-image network. The network 205 includes twenty-four initial feature maps, a growth rate of twenty-four and two levels of pooling. The network 205 produces a probability output from a SoftMax activation layer at each step of the recurrent process. The probability output maps 207 obtained at a given step are used as context information for a subsequent iteration. The network 205 includes as many input channels as output channels, e.g. one per class of the segmentation problem. In an example, there are two output channels and two input channels. A first output channel may correspond to the brain and the second one for non-brain data. At an initial step, a volume is provided on each input channel. After each process iteration, probability output maps are multiplied with the input data and input back to the network for the next iteration. Each volume provided on the different input channels is thus a subset of the full input volume, that can be summed up to obtain the original full volume.

Figure 4B:
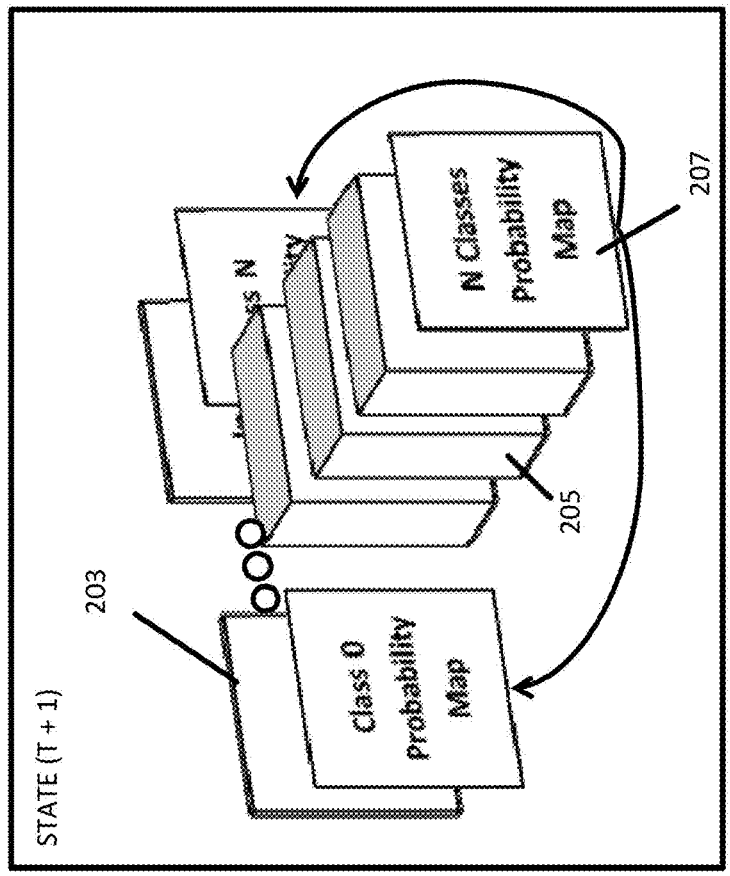
FIGS. 4A and 4B depict example diagrams of two states of the recursive training of FIG. 3.
Figure 4A:
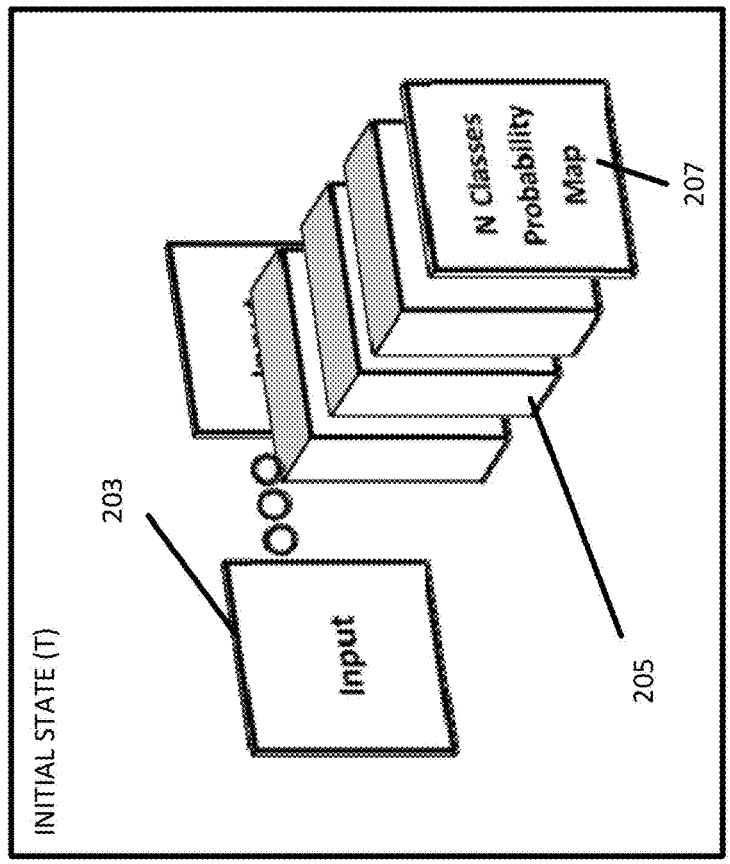

FIGS. 4A and 4B depicts an initial state (T) and a subsequent state (T+1) in the iterative process. Both FIGS. 4A and 4B include an input 203, the network 205, and the output probability maps 207. For the initial state, an MR volume 203 from a set of training data 201 is input into the network 205. At each state T, the network 205 takes new inputs 203 that will be related to the previous time step T−1. The network 205 includes as many input channels (N) as there are classes in the problem. At state T, each channel will take the input X multiplied by the probability map 207 of each segmented class obtained at step T−1 (the input is only X at T=0). FIG. 4A depicts an initial state (T) where the only inputs are the original inputs 203. FIG. 4B depicts a state (T+1) where the input is the original input multiplied by the probability map of the previous state (T).

Referring back to FIG. 3, the generated score is also used by the reinforcement agent 215. For each iteration, the input volume 203 may also be up sampled, down sampled, or pooled to change the resolution. The decision of whether to up sample, down sample, or pool the resolution may be performed by a reinforcement agent 215 or may selected randomly. The reinforcement agent 215 generates a resolution action 217 to be performed on the volume to be input to the network 205 for a subsequent iteration. The action is whether to work at lower, higher or same resolution (e.g. apply a pooling or an up-sampling action to the next input volume). The reinforcement agent 215 may use reinforcement learning to select the resolution action 217. Reinforcement learning provides a mechanism to identify immediate solutions given a long-term goal. Reinforcement learning may be described using the concepts of agents, environments, states, actions and rewards. The reinforcement agent 215 is an agent that takes actions, e.g. selects the resolution action 217 of how to change the resolution for the next state of the training process. The agent may decide to up sample, pool, down sample, or take no action. The magnitude of up sampling and down sampling may also be selected by the agent. The state of the iterative process is the current situation or current environment that the agent is acting on. In an example, the state may be the difference between the output 209 and the input data 203 of the network 205. The agent 215 will output an action 217 to take on the combination of the output 209 and the input data 203, and feed the segmentation network for the new step. A reward is the feedback by which the process measures the success or failure of an agent's actions. From any given state, an agent sends output in the form of actions to the environment, and the environment returns the agent's new state (that resulted from acting on the previous state) as well as rewards, if there are any. Rewards may be immediate or delayed. Rewards effectively evaluate the agent's action. A reward may be calculated from a DICE score 211 in a final resolution obtained from the segmentation. A policy may be provided to guide the strategy that the agent employs to determine the next action based on the current state. It maps states to actions, the actions that promise the highest reward.

The reinforcement agent 215 identifies the environment based on the output of the network 205. The reinforcement agent 215 selects a resolution action 217 for how to adjust the resolution of the next input as function of a defined policy. The result of the resolution action 217 is measured by a score 211 of a final resolution of the segmentation. A reward is provided for the resolution action 217 that provides additional feedback for the agent to identify future resolution actions 217.

For each iteration, the resolution action 217 is performed on the MR volume data in addition to the multiplication by the probability maps 207. The change in resolution to the input provides a mechanism for the network 205 to learn how to generate accurate segmentation regardless of the resolution of the input volume.

The process is repeated for a number of iterations. A predefined number of iterations may be performed for each input volume from the training data 201. In an example, five, ten, twenty, or more iterations may be used. Each iteration takes the output probability maps 207 and the input volume and multiplies the output probability maps 207 and copies of the input volumes together to generate the input channels for the current state. The number of iterations may be selected as a tradeoff between performance and time constraints. More iterations may produce a more accurate network 205 but may take long to train.

After the iterative process is finished, another volume is provided from the training data 201. The recursive process is then performed on the new volume. This is repeated until all volumes in the training data 201 set have been processed or the network 205 is determined to be trained.

Figure 5:
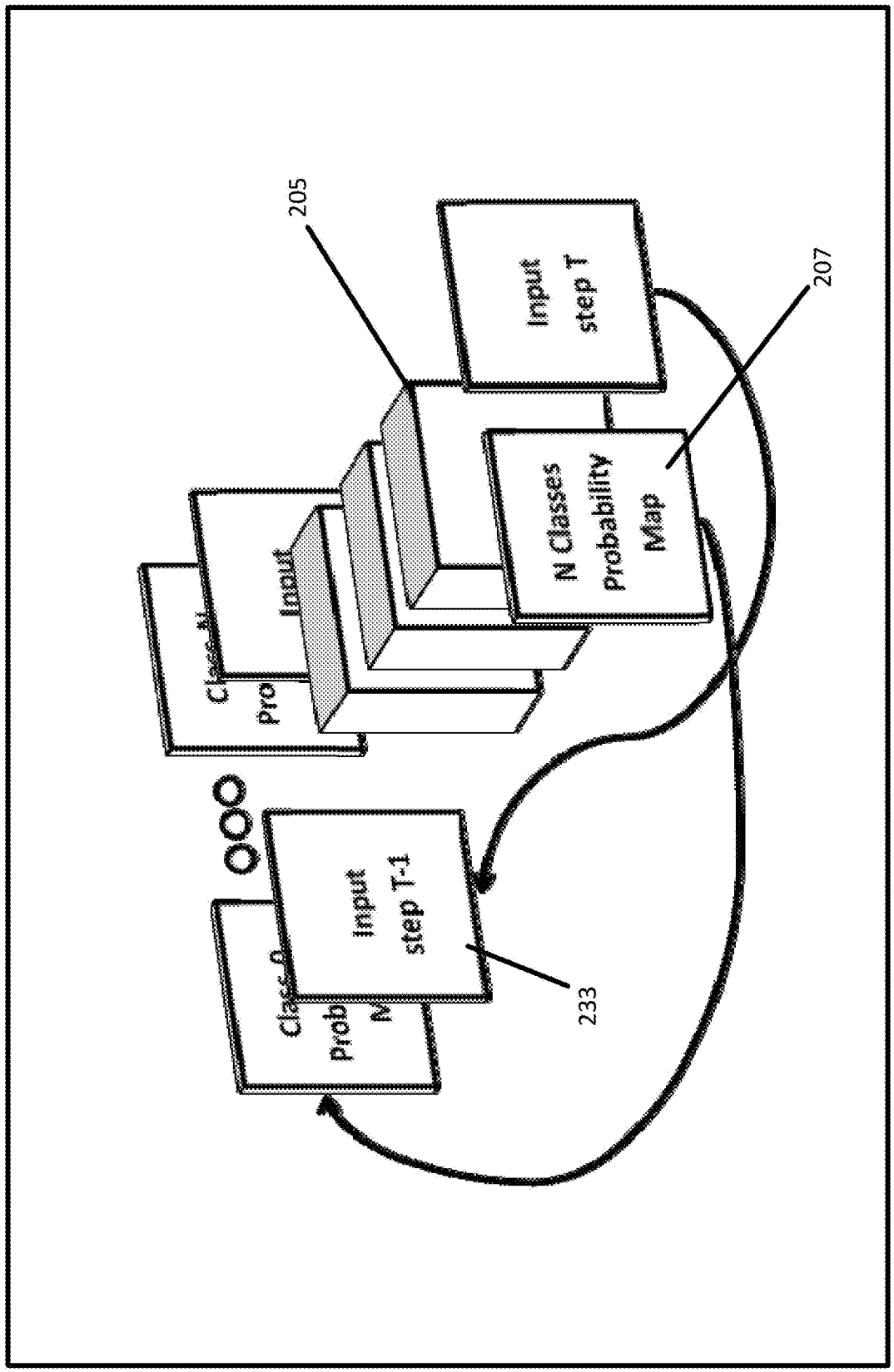
FIG. 5 depicts an example diagram for recursively training a network.

In an embodiment, the network 205 may also be hardened against the different data distribution problem that arises due to contrast variations. Data normalization may be performed prior to inputting the training data 201 into the network 205. Normalization may include normalizing all the input volumes 203 to the same dimensions. Additionally, or alternatively, in addition to segmenting the input data 203, the network 205 may output an image or volume that is used as input at a subsequent step t+1 instead of reusing the original image or volume. For the process to converge properly, multiple steps are performed before updating the network 205, as the network 205 learns the input recursively. The model normalizes its input over iterations, to extract necessary features for the final segmentation. FIG. 5 depicts an example of using an output image as the input image for a subsequent iteration. Similar to FIG. 4B, FIG. 5 includes the network 205 and the probability maps 207. The input to the network 205, however, is not the original volume from the training data set, but rather a volume 233 generated at the last iteration (T−1) by the network. The network 205 inputs the volume 233 and output another volume that will be used for the input at (T+1). By reinjecting a predicted input through the input to the network may be automatically normalized.

Once the network 205 is trained, the trained network 305 may be applied. The trained network 305 with defined or learnt features is used to extract features from previously unseen input MR data. The trained network 305 extracts values for features from the acquired MR data with or without other information to generate a segmented image.

Figure 6:
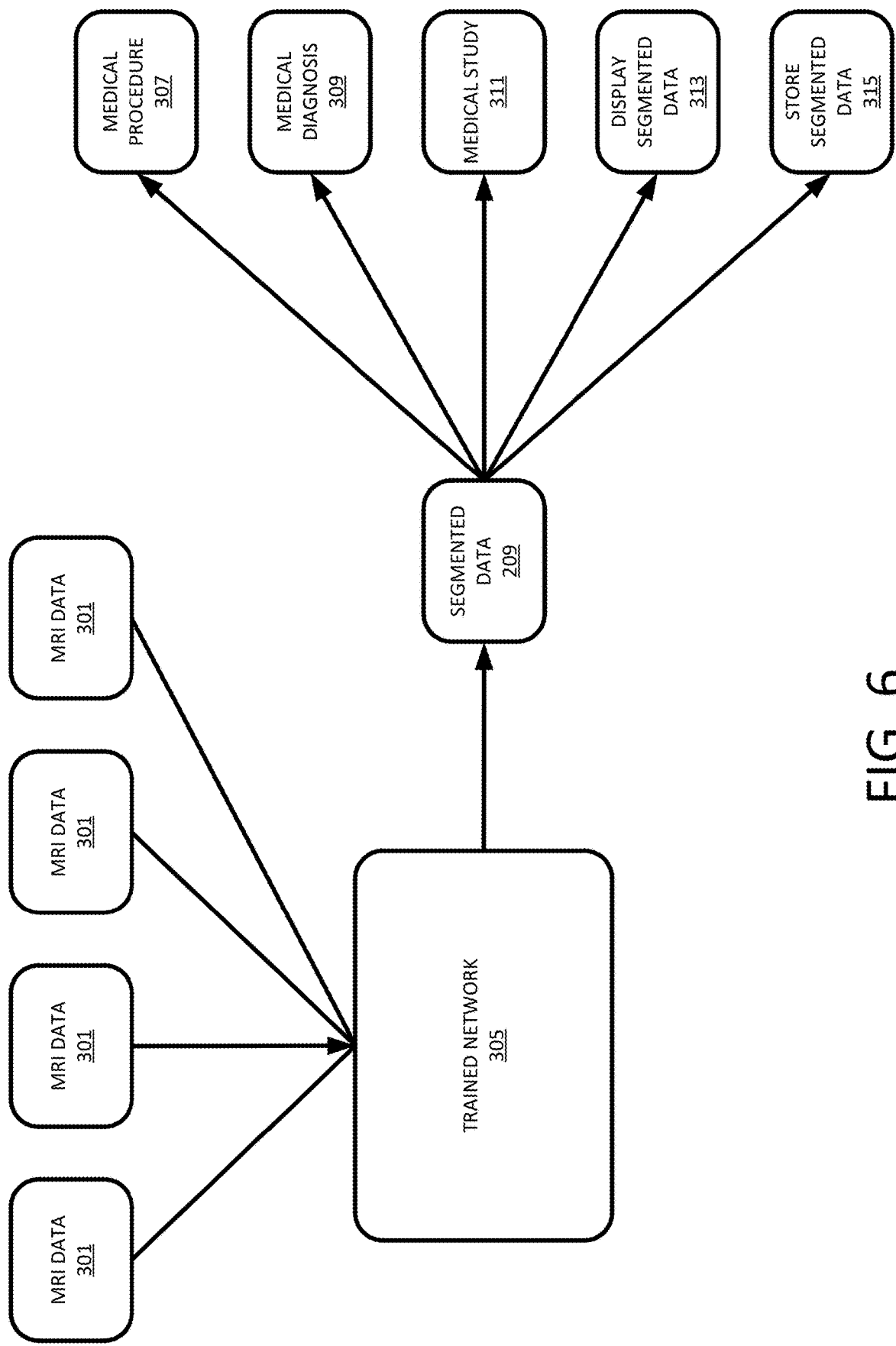
FIG. 6 depicts an example flowchart for applying a trained network.

FIG. 6 depicts an example workflow for generating segmented medical data for uses in medical diagnosis, prognosis, planning, treatment, or analysis. The acts are performed by the system of FIG. 1, FIG. 5, FIG. 8, other systems, a workstation, a computer, and/or a server. Additional, different, or fewer acts may be provided. The trained network 305 may be used for any segmentation task. The examples below use medical imaging data and more specifically skull stripping, but other types of image data may be segmented. The examples use three-dimensional volumes but the acts may be applied to two-dimensional images. The acts are performed in the order shown (e.g., top to bottom) or other orders.

At 301, an object is scanned by the magnetic resonance imaging system to acquire MR data 301. As depicted and described in FIG. 1 above, the MR data 301 may be acquired using an MR scanner. For example, gradient coils, a whole-body coil, and/or local coils generate a pulse or scan sequence in a magnetic field created by a main magnet or coil. The whole-body coil or local coils receive signals responsive to the re-orientation of molecules shifted due to the scan sequence. In an embodiment and used as an example below, the MR data may represent image data for a brain of a patient. Different objects, organs, or regions of a patient may also be scanned.

The MR data 301 is k-space data or image data. Image data may be MR data 301 after Fourier transform into object space. The image data may be at any point after transform, so may be scalar values or may be formatted as RGB values for a display screen. The MR data 301 may be scan data to be used to generate an image on a display. The acquired MR data 301 may be data being processed to generate an image, data formatted for display, or data that has been used to display. The MR data 301 may be data with no or some image processing.

In an embodiment and used as an example below, the MR data 301 may represent a volume. A three-dimensional dataset is obtained. As k-space data, information content may be provided that is responsive to a three-dimensional distribution of locations, but the data itself does not directly represent the locations prior to transform. In alternative embodiments, a two-dimensional dataset representing or responsive to tissue in a plane is obtained. In other embodiments, sequences of MR data responsive to the same tissue over time are acquired for training.

Alternative methods may be used to acquire the MR data 301. The MR data 301 may be acquired remotely from the server or workstation or may be acquired at a different time, for example, hours or days prior to the processing provided below. The MR data may be stored locally onsite or offsite, for example in the cloud.

The MR data 301 may be acquired at different resolutions. For example, one set of MR data may be 256×256×256 while another may be 128×128×32. The MR data 301 may be normalized to a standard dimension. The trained network 305 may be configured to input a standard dimensional image or volume. The MR data 301 may be converted to the standard dimension. If, for example, the MR data 301 is too dimensionally small, the MR data 301 may be up sampled to the standard dimensions.

At 303, the MR data 301 is input into a trained network 305. The trained network 305 is configured to input multiple different resolutions of MRI data 301 that result from different types of protocols, sequences, or scans. Rather than pre-programming the features and trying to relate the features to attributes, the deep architecture of the network is defined to apply the features at different levels of abstraction based on an input image data with or without pre-processing. The features were learned to reconstruct lower level features (i.e., features at a more abstract or compressed level). For example, features for reconstructing an image were learned. For a next unit, features for reconstructing the features of the previous unit were learned, providing more abstraction. Each node of the unit represents a feature. Different units are provided for learning different features.

The trained network 305 may be a dense image-to-image network trained to generate a segmented image given MR data. The network 205 is trained offline, e.g. prior to the acts of FIG. 6. The training process includes recursively training the network 205 using different resolutions. The different resolutions are selected using a reinforcement agent 215. The network 205 is trained recursively by using an output of the network 205 in combination with a change in resolution as the input to a subsequent iteration. During the recursive process, the network 205 is adjusted using back propagation in order to generate a more accurate segmented output. The recursive process for an input volume ends after a number of iterations. The process is repeated for each volume in the training data 201. The training process produces a trained network 305 that is configured to generate accurate segmentations regardless of the resolution of the input volume.

Figure 7:
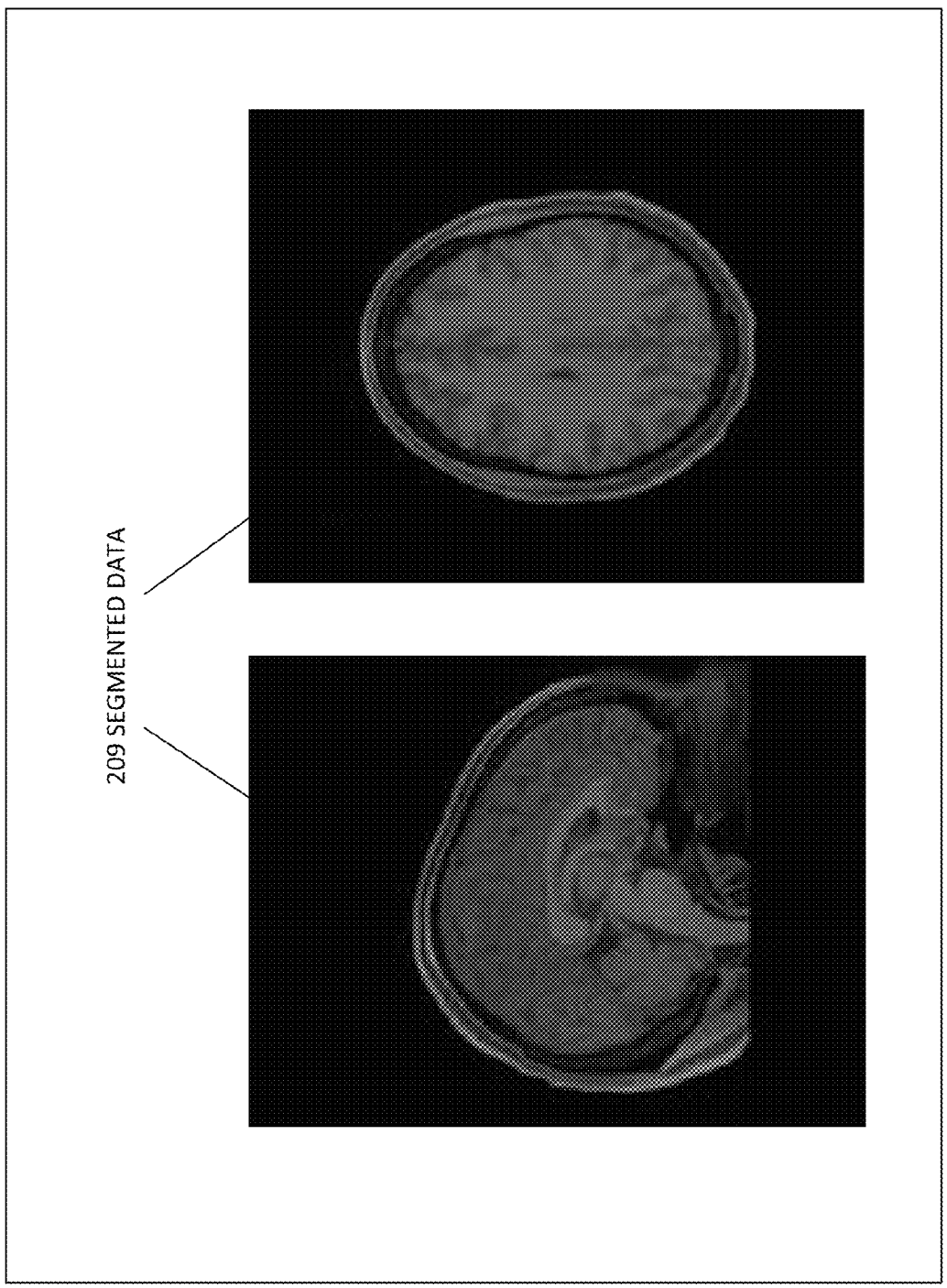
FIG. 7 depicts two example of output segmented data from a network.

The trained network 305 generates segmented data from the input MR data 209. The segmented data 209 may include boundaries for different types of classes. For example, for skull stripping, the output image or volume may include designations for brain tissue or non-brain tissue. FIG. 7 depicts two examples of segmented data output 209 by the trained network 305 and overlaid over the original images. In FIG. 7, the brain tissue is highlighted while the non-brain tissue is ignored. In another example of segmented data 209 for a brain, boundaries and classifications may be included for at least white matter, grey matter, and cerebrospinal fluid. Each pixel or voxel may be classified as a type of tissue. The output image may identify the type of tissue depicted in the image. Different colors or shades of grey, for example, may be used to depict the segmented image. The output image may be annotated with additional information.

At 305, the trained network 305 outputs the segmented data 209. The output segmented data 209 may be used for different procedures or diagnosis. For example, the output segmented data may be displayed 313 to an operator or physician. The output may be presented to an operator with labels or different colors representing different tissues or points of interest. The output may be two-dimensional or a rendering from a three-dimensional distribution. The output may be color or black and white. The image data and the segmented data may be stored 315 for later use.

In a skull stripping example and other examples, further processing may be performed once the non-brain tissue has been removed from the images. The removal of the non-brain tissue allows the further processing or analysis to proceed without having to deal with possible overlapping intensities between the brain and non-brain tissue resulting in fewer computational resources being used, a shorter turnaround time, and more accurate results. The segmented data 209 may be used for medical procedures 307, medical diagnosis 309, or medical studies 311 before or after additional processing.

FIG. 8 depicts one embodiment of a control unit for generating segmented images from MR data. The control unit includes an image processor 22, a memory 24, and a display 26. The control unit 20 may be connected with a server 28 and an MR imaging device 36. Additional, different, or fewer components may be provided. For example, network connections or interfaces may be provided, such as for networking between the control unit 20 and server 28. A workstation with a user interface may be provided for an operator to input data.

The MR imaging device 36 may be similar to the MR imaging device 36 as depicted in FIG. 1. The MR imaging device 36 is configured to acquire MR data that may be processed into one or more images or volumes by the control unit 20. The control unit 20 may provide commands to the MR imaging device 36. Alternatively, the MR imaging device 36 may function entirely on its own without any input from the control unit 20.

The image processor 22 (or processor) is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for processing an image. The processor 22 is a single device or multiple devices operating in serial, parallel, or separately. The processor 22 may be a main processor of a computer, such as a laptop or desktop computer, or may be a processor for handling some tasks in a larger system, such as in the MR system. The processor 22 is configured by instructions, design, hardware, and/or software to perform the acts discussed herein.

The server 28 may be co-located with the control unit 20 or may be located remotely. The server 28 may connect to the MR system 100 or control unit 20 via a network. The network is a local area, wide area, enterprise, another network, or combinations thereof. In one embodiment, the network is, at least in part, the Internet. Using TCP/IP communications, the network provides for communication between the processor 24 and the server 28. Any format for communications may be used. In other embodiments, dedicated or direct communication is used.

The server 28 may include the processor 24 or group of processors. More than one server 28 or control unit 20 may be provided. The server 28 is configured by hardware and/or software. In one embodiment, the server 28 performs ML of the network 205. The server 28 may acquire and the memory 24 may store MR data from multiple different MR systems.

The processor 24 and/or server 28 are configured to perform the acts discussed above for generating segmented images. The processor 24 and/or server 28 may access and implement the code stored in memory 24.

The memory 24 may be a graphics processing memory, a video random access memory, a random-access memory, system memory, cache memory, hard drive, optical media, magnetic media, flash drive, buffer, database, combinations thereof, or other now known or later developed memory device for storing data or video information. The memory 24 is part of the control unit 20, part of a database, part of another system, a picture archival memory, or a standalone device. The memory 24 may store image data from the MR device 36. The memory 24 may store an instruction set or computer code configured to implement the network 205.

The memory 24 includes an instruction set or computer code for implementing the network 205. In an embodiment, the memory 24 includes a trained network 305 and training data 201. In an embodiment, only the trained network 305 is stored in memory 24. The trained network 305 may be configured to input an MR volume and output a segmented MR volume. The trained network 305 may be configured to function regardless of the resolution of the input MR volume. To provide resolution independent segmentation, a network 205 is trained recursively and with a reinforcement agent 215. For an initial state, the network 205 takes as input a volume or image from a training set of data. The network 205 generates a plurality of probability maps 207. The number of probability maps 207 matches the number of classes that also matches the number of input channels to the network 205. For subsequent states, the network 205 takes as input the volume or image multiplied by the probability maps 207 generated at the previous state. In addition, the volume or image is up sampled or pooled to changes the resolution of the volume or image. The decision to up sample or pool the volume or image may be determined using a reinforcement agent 215 trained using a reinforcement mechanism. The reinforcement mechanism may generate a reward for the reinforcement agent 215 based on a comparison score between the output of the network 205 and ground truth/gold standard data.

The memory 24 or other memory is alternatively or additionally a non-transitory computer readable storage medium storing data representing instructions executable by the programmed processor 22 for generating resolution independent segmented data. The instructions for implementing the processes, methods and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code, and the like, operating alone, or in combination. Likewise, processing strategies may include multiprocessing, multitasking, parallel processing, and the like.

The display 26 may be configured to display images to an operator. The display 26 may augment the images with additional information or overlays. The display 26 may be configured to display the images in two dimensions, three dimensions, or, for example, in augmented or virtual reality scenarios.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A method for generating segmented magnetic resonance volumes in a magnetic resonance imaging system, the method comprising:
scanning a patient by the magnetic resonance imaging system; magnetic resonance volume data resulting from the scanning;
inputting the magnetic resonance volume data to a machine trained network that is recursively trained using machine learning techniques to generate segmented volumes from input magnetic resonance volume data regardless of a resolution of the input magnetic resonance volume data, wherein recursively training the network comprises generating probability maps from a SoftMax activation layer at each iteration of the recursive training, up-sampling or pooling the input volume to different resolutions for each iteration, and after each iteration multiplying the probability maps with the up-sampled or pooled input volume and inputting the multiplied probability maps back to the network for subsequent iteration;
generating, by the machine trained network, a segmented magnetic resonance volume from the input magnetic resonance volume data; and
displaying the segmented magnetic resonance volume.

2. The method of claim 1, wherein the machine trained network is a three-dimensional image-to-image network.

3. The method of claim 1, wherein the magnetic resonance imaging system is configured to acquire magnetic resonance volume data of a brain of a patient.

4. The method of claim 3, wherein the machine trained network is trained to perform a segmentation task comprising skull stripping of the magnetic resonance volume data.

5. The method of claim 4, further comprising:
performing a subsequent segmentation of the segmented magnetic resonance volume to identify tissue types.

6. A method for training a network using machine learning to generate segmented magnetic resonance images regardless of input resolution, the method comprising:
inputting a magnetic resonance image of a plurality of magnetic resonance images of a set of training data into a network using a quantity of input channels, wherein the quantity is equal to a quantity of classifications provided by the network;
generating, by the network, a segmented image including a quantity of probability maps equal to the quantity of classifications, wherein each probability map of the quantity of probability maps comprises a probability map for a different class of the quantity of classifications;
comparing the segmented image to a ground truth segmented image for the magnetic resonance image;
adjusting the network based on the comparison;
selecting, by a reinforcement agent, a resolution action as a function of the comparison;
multiplying each of the quantity of input channels of the magnetic resonance image by a respective probability map of the quantity of probability maps;
performing the resolution action on the magnetic resonance images for each of the quantity of input channels;
inputting the altered magnetic resonance images of the quantity of input channels into the network;
repeating generating, comparing, adjusting, selecting, multiplying, performing, and inputting for at least five iterations; and
outputting a machine trained network.

7. The method of claim 6, wherein the network is a dense image to image network.

8. The method of claim 6, wherein the resolution action comprises one of up sampling, pooling, or no action.

9. The method of claim 6, wherein the network is configured to input a magnetic resonance brain image and output a segmented magnetic resonance brain image.

10. The method of claim 6, wherein the reinforcement agent is trained using a reinforcement mechanism to select the resolution action.

11. The method of claim 6, wherein the segmented image is used as the input for a subsequent iteration.

12. The method of claim 6, wherein generating, comparing, adjusting, selecting, multiplying, performing, and inputting is repeated for at least ten iterations.

13. The method of claim 6, wherein each magnetic resonance image of the plurality of magnetic resonance images of the set of training data is input into the network prior to outputting the machine trained network.

14. A system for generating a machine trained network configured to use inputs of different resolutions, the system comprising:
a magnetic resonance imaging system configured to acquire magnetic resonance data at different resolutions;
a memory configured to store the magnetic resonance data, associated labeled magnetic resonance data, and a network; and
an image processor configured to recursively train the network using an input volume from the magnetic resonance data and an associated labeled volume using back propagation;
wherein the network generates probability maps from a SoftMax activation layer at each iteration of the recursive training;
wherein the input volume is up sampled or pooled to different resolutions for each iteration;
wherein after each iteration, the probability maps are multiplied with the input volume and input back to the network;
wherein the recursive training is repeated for each volume in the magnetic resonance data.

15. The system of claim 14, wherein the network is configured to input a magnetic resonance brain volume and output a segmented magnetic resonance brain volume regardless of the resolution of the input magnetic resonance brain volume.

16. The system of claim 14, wherein the image processer is further configured to select whether the input volume is up sampled or pooled to different resolutions for each iteration as a function of a selection by a reinforcement agent stored in the memory.

17. The system of claim 16, wherein the reinforcement agent selects whether the input volume is up sampled or pooled to different resolutions for each iteration as a function of a comparison between an output of the network and an associated labeled volume at each iteration.

18. The system of claim 14, wherein the network is a three dimensional dense image to image network.

19. The system of claim 14, wherein the image processor is configured to perform at least five iterations of the recursive training for each volume in the magnetic resonance data.

* * * * *